US008442293B2

(12) United States Patent
Bruder et al.

(10) Patent No.: US 8,442,293 B2
(45) Date of Patent: May 14, 2013

(54) CT IMAGE RECONSTRUCTION IN THE EXTENDED FIELD OF VIEW

(75) Inventors: Herbert Bruder, Höchstadt (DE); Thomas Flohr, Uehlfeld (DE); Rainer Raupach, Heroldsbach (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 186 days.

(21) Appl. No.: 13/018,724

(22) Filed: Feb. 1, 2011

(65) Prior Publication Data

US 2011/0188723 A1    Aug. 4, 2011

(30) Foreign Application Priority Data

Feb. 2, 2010  (DE) .......................... 10 2010 006 585

(51) Int. Cl.
 *G06K 9/00* (2006.01)
 *A61B 6/00* (2006.01)

(52) U.S. Cl.
 USPC .............................. 382/131; 382/199; 378/4

(58) Field of Classification Search ............... 382/100, 382/103, 106–107, 128–134, 154, 155, 162, 382/168, 171–173, 181, 194, 199, 221, 232, 382/254, 266, 274, 276, 286–298, 305, 312; 378/4, 15, 8, 21; 345/424
 See application file for complete search history.

(56) References Cited

U.S. PATENT DOCUMENTS

| | | | | |
|---|---|---|---|---|
| 5,270,926 A | * | 12/1993 | Tam | 378/4 |
| 6,130,930 A | * | 10/2000 | Tam | 378/4 |
| 6,442,288 B1 | * | 8/2002 | Haerer et al. | 382/128 |
| 6,720,966 B2 | * | 4/2004 | Barth et al. | 345/424 |
| 6,850,587 B1 | * | 2/2005 | Karimi et al. | 378/15 |
| 7,054,406 B2 | * | 5/2006 | Ikeda et al. | 378/8 |

FOREIGN PATENT DOCUMENTS

DE    102007041459 A1    3/2009

OTHER PUBLICATIONS

Efficient Extended Field of View (eFOV) REconstruction Techniques for Multi-Slice Helical CT, H. Bruder, C. Suess, K. Stierstorfer, Physics of Medical Imaging, SPIE Medical Imaging, Proceedings 2008, vol. 9, No. 30, E2-13; Magazine; 2008; DE.
German language Office Action dated Dec. 3, 2010 for German Patent Application No. DE 10 2010 006 585.4 (not yet published).
German Patent Application No. DE 10 2010 006585.4 filed Feb. 2, 2010 (not yet published).

* cited by examiner

*Primary Examiner* — Seyed Azarian
(74) *Attorney, Agent, or Firm* — Harness, Dickey & Pierce, PLC

(57) ABSTRACT

A method is disclosed for reconstructing image data of an examination subject from measured data, wherein the measured data was acquired in the course of a relative rotational movement between a radiation source of a computed tomography system and the examination subject. A limited area between the radiation source and a detector represents a field of view in respect of which measured data can be acquired, and parts of the examination subject were located at least temporarily outside the field of view in the course of the measured data acquisition. In at least one embodiment, first image data is reconstructed from the measured data, and a boundary of the examination subject is determined with the aid of the first image data. The first image data is subsequently modified using the determined boundary, and projection data is calculated from the modified first image data. The measured data is modified using the projection data, and finally second image data is reconstructed from the modified measured data.

36 Claims, 5 Drawing Sheets

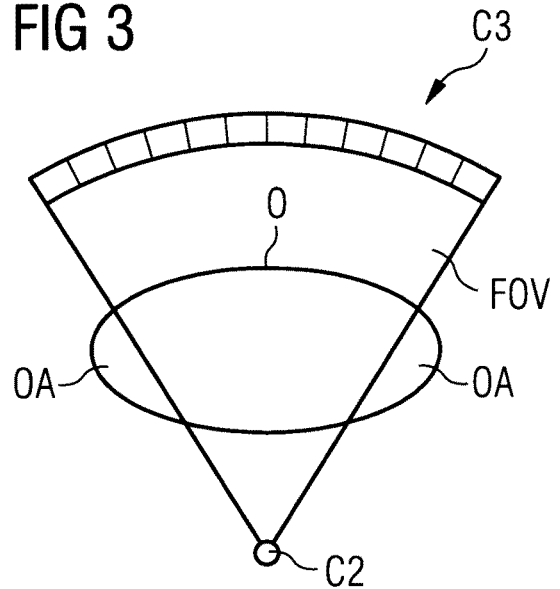
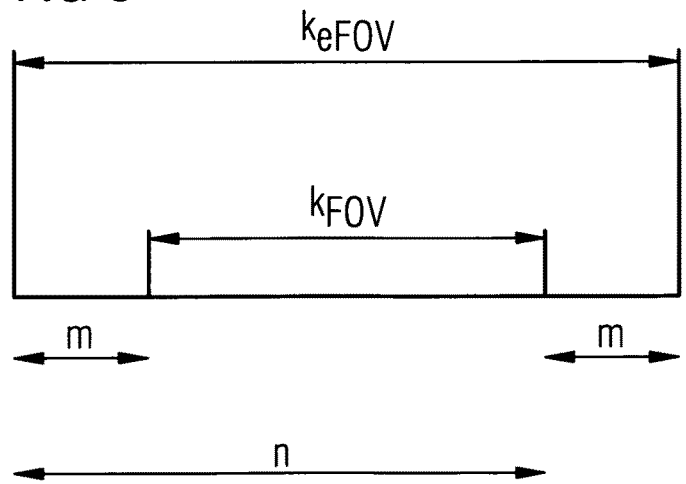

FIG 4
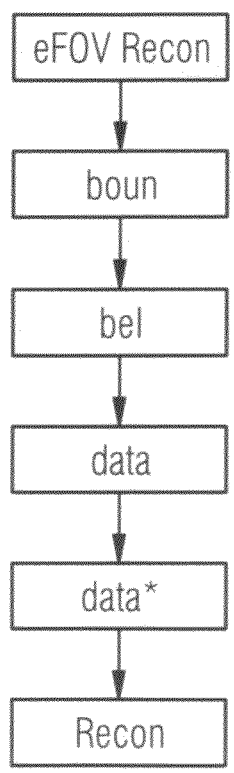
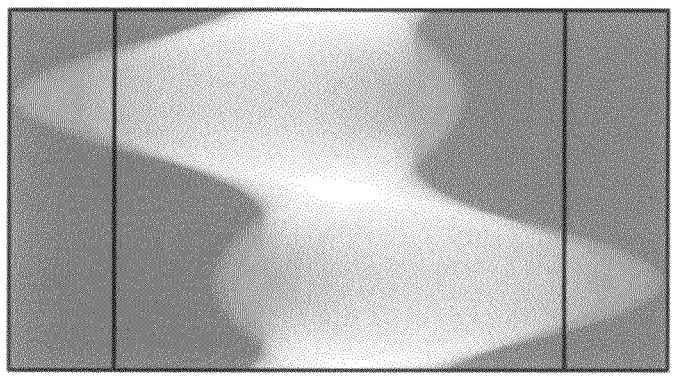

CT IMAGE RECONSTRUCTION IN THE EXTENDED FIELD OF VIEW

PRIORITY STATEMENT

The present application hereby claims priority under 35 U.S.C. §119 on German patent application number DE 10 2010 006 585.4 filed Feb. 2, 2010, the entire contents of which are hereby incorporated herein by reference.

FIELD

At least one embodiment of the invention generally relates to a method for reconstructing image data of an examination subject from measured data, wherein the measured data was acquired by a computed tomography system and during the measurement parts of the examination subject were located at least temporarily outside the field of view.

BACKGROUND

Methods for scanning an examination subject by way of a CT system are generally known. For example, typical methods employed in such cases are circular scans, sequential orbital scans with patient feed-through, or spiral scans. Other types of scan that are not based on circular movements are also possible, such as e.g. scans with linear segments. Absorption data of the examination subject is recorded from different recording angles with the aid of at least one X-ray source and at least one oppositely located detector, and said thus collected absorption data or, as the case may be, projections are computed by means of appropriate reconstruction methods into sectional images (slices) through the examination subject.

In order to reconstruct computed tomographic images from X-ray CT data sets of a computed tomography device (CT scanner), i.e. from the acquired projections, a technique referred to as filtered back-projection (FBP) is currently employed as the standard method. Following the data acquisition a so-called "rebinning" step is performed in which the data generated by means of the beam spreading out from the source in the shape of a fan is reordered in such a way that it is available in a form as though the detector had been impinged upon by X-ray beams converging in parallel onto the detector. The data is then transformed into the frequency domain. Filtering takes place in the frequency domain and subsequently the filtered data is back-transformed. A back-projection onto the individual volume elements or "voxels" within the volume of interest is then performed with the aid of the thus re-sorted and filtered data.

A limited range of measurement, the field of view, is present due to the extent of the detector. This means that at a certain projection angle, projection and/or measured data can be acquired only for those voxels of an examination subject which lie within the field of view. Often, however, the problem arises that the extent of the examination subject is such that not all parts of the examination subject are located within the field of view during the entire period of measured data acquisition. This results in measured data sets that are incomplete in respect of said parts of the examination subject and consequently leads to artifacts being produced during the image reconstruction.

SUMMARY

In at least one embodiment of the invention, a method is disclosed for reconstructing CT images from measured data, wherein it is to be taken into account that the examination subject extends outside (exceeds) the field of view. It is also proposed, in at least one embodiment, to disclose a corresponding control and computing unit, a CT system, a computer program, and/or a computer program product.

Methods are disclosed, as well as a control and computing unit, a CT system, a computer program, and a computer program product having features recited in additional independent claims. Advantageous embodiments and developments are the subject matter of dependent claims.

With at least one embodiment of the inventive method for reconstructing image data of an examination subject from measured data, the measured data was acquired beforehand in the course of a relative rotational movement between a radiation source of a computed tomography system and the examination subject. Due to the limited extent of the detector a limited area between the radiation source and the detector represents a field of view in respect of which measured data can be acquired. However, parts of the examination subject were located at least temporarily outside the field of view during the measured data acquisition. A reconstruction of first image data from the measured data is performed. A boundary of the examination subject is determined with the aid of the first image data. The first image data is modified using the determined boundary. Projection data is calculated from the modified first image data. The measured data is modified using projection data, and second image data is reconstructed from the modified measured data.

The examination subject is too large for the field of view of the CT scanner. This means that—depending on the projection angle, i.e. on the position of the X-ray source relative to the examination subject—more or less large parts of the examination subject will not lie within the field of view, with the result that no data acquisition in respect of these parts can take place for the respective projection angle. An incomplete measured data set will therefore be present for some voxels of the examination subject. This incompleteness of the measured data leads to artifacts, including for those parts of the examination subject which were located in the field of view throughout the entire period of the data acquisition. In order to reduce the undesired effect on the images to be reconstructed resulting from the incompleteness of the measured data due to the field of view being exceeded, not just a single, but a double image reconstruction is performed according to the invention.

The result of the first image reconstruction is used in order to determine a boundary of the examination subject. With the aid of the boundary it can be recognized which pixels belong to the examination subject: the pixels contained within the boundary are to be attributed to the examination subject, those outside the boundary to the subject's environment or to another object. In the case of a patient the boundary to be determined corresponds to his/her skin or the surface of his/her clothes. The examination subject can, of course, also be part of a larger object, such as e.g. a tumor or an organ of a patient. Image processing methods known per se can be resorted to for determining the boundary and applied to the first image data. The determined boundary can be total or partial; it can be composed of a plurality of segments.

The determined boundary is subsequently used for modifying the first image data. This modification preferably relates only to a subset of the first image data; however, a revision of all of the first image data is also possible. The first image data modified in such a way is used in order to compute projection data. The projection data constitutes synthetic or, as the case may be, computed measured data; from said data it is therefore possible to derive which measured data would lead to the modified first image data in an image reconstruction. While the image data is obtained from the measured data and projection data by means of an image reconstruction algorithm, a forward projection leads from the image data to the projection data.

The projection data is used in order to modify the measured data. In the simplest case the modification can be equivalent to a supplementing of the measured data so that the incompleteness of the measured data that is due to the field of view being exceeded is rectified. Furthermore it is also possible for the measured data to be modified in addition to or as an alternative to being supplemented.

The modified measured data is subsequently used as a basis for an image reconstruction. The resulting second image data is better than the first image data because it is based, not on the original, but on the modified measured data, into which knowledge of the boundary of the examination subject has already been incorporated.

In a development of at least one embodiment of the invention a method for image reconstruction in the extended field of view is used for reconstructing the first image data. Such methods may already be known per se and already take into account that a field of view has been exceeded. Methods of this kind lead to better image reconstruction results than algorithms which take no account of the exceeding of the field of view. In this way, with the first image data as the starting point for the subsequent method, use is already being made of enhanced image data compared to simple image reconstruction methods.

It is particularly advantageous, in the course of the modification of the first image data, to change values of pixels contained within the determined boundary and outside the field of view. The pixels are therefore those parts of the examination subject for which incomplete measured data was present due to the field of view having been exceeded. In respect of these pixels it is possible to change only some or all of the pixel values. The change can consist in assigning a constant value to the pixel values, e.g. the HU value of water. Preferably only the pixel values of the pixels contained within the determined boundary and outside the field of view are changed in the course of the modification of the first image data. This means not changing those pixels of the examination subject for which complete measured data is present, i.e. pixels which were located within the field of view throughout the entire measurement.

According to an embodiment of the invention the boundary of the examination subject is determined using a threshold value comparison of pixel values of the first image data. A suitably chosen threshold value permits a distinction to be made as to whether the respective pixel is to be assigned to the examination subject or to the latter's environment or, as the case may be, to some other object.

The modification of the measured data serves to create a data set which is used as data on which the reconstruction of the second image data is to be based. Candidates suitable for consideration as a usable variable in this case are in particular the original measured data and the projection data.

In a development of at least one embodiment of the invention the respective projection data is used in the course of the modification of the measured data for at least one area outside the detector as data on which the reconstruction of the second image data is to based. This is equivalent to a supplementing of the measured data, for the measured data can only be acquired by the detector; naturally no measured data is available for areas outside the detector. It is therefore specified through the supplementing process that data has also been acquired outside the detector and said data can be used for the image reconstruction.

In addition or alternatively it is possible, in the course of the modification of the measured data for at least one area of the detector, to regard the respective measured data as data on which the reconstruction of the second image data is to be based. This means that there are one or more areas within the detector whose measured data is not modified. Rather, this data is used unmodified as a basis for the image reconstruction of the second image data. The central region of the detector is particularly suitable for this purpose. It is, however, also possible not to modify the measured data for the entire area of the detector, but to use it as a basis for the reconstruction of the second image data in the same form as for reconstructing the first image data. This would mean simply supplementing the measured data, not changing its values.

In addition or alternatively it is possible, in the course of the modification of the measured data for at least one area at the edge of the detector, to regard a combination of the respective measured data and the respective projection data as data on which the reconstruction of the second image data is to be based. A combination of this kind is preferably calculated as a weighted total. Preferably the weighting is applied in such a way that the measured data gains in weight relative to the projection data with increasing distance from the edge of the detector. A $\cos^2$ function, for example, is suitable as a weighting function.

The control and computing unit according to at least one embodiment of the invention serves for reconstructing image data of an examination subject from measured data acquired by a CT system. The unit includes a program memory for storing program code, there being resident herein—possibly inter alia—program code that is suitable for performing a method of the above-described type. The CT system according to at least one embodiment of the invention includes such a control and computing unit. In addition it can include other component parts that are required e.g. for the purpose of acquiring measured data.

The computer program according to at least one embodiment of the invention possesses program code segments that are suitable for performing the method of the above-described type when the computer program is executed on a computer.

The computer program product according to at least one embodiment of the invention comprises program code segments stored on a computer-readable data medium that are suitable for performing the method of the above-described type when the computer program is executed on a computer.

BRIEF DESCRIPTION OF THE DRAWINGS

The invention is explained in more detail below with reference to an example embodiment and the attached drawings, in which:

FIG. 3: shows a section of the recording geometry normal to the z-direction, FIG. 4: shows a flowchart, FIG. 5: is an illustration to aid understanding of the formulae (1) and (2)

DETAILED DESCRIPTION OF THE EXAMPLE EMBODIMENTS

Figure 1:
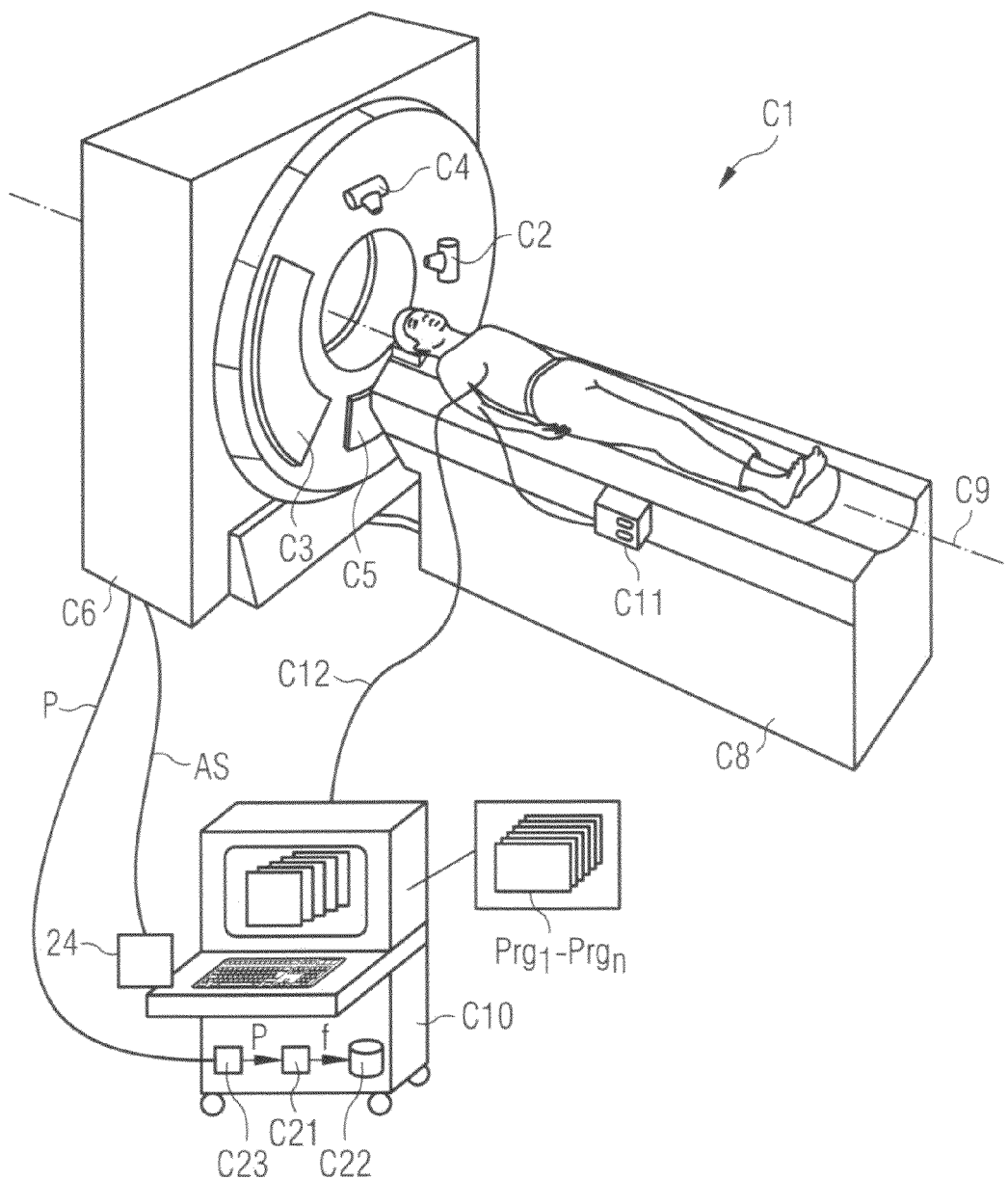
FIG. 1: shows a first schematic representation of an example embodiment of a computed tomography system having an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 firstly shows a schematic representation of a first computed tomography system C1 having an image reconstruction device C21. The CT system in this case is a CT scanner of the so-called third generation, though the embodiments of the invention is not limited thereto. Located in the gantry housing C6 is a closed gantry (not shown here) on which is disposed a first X-ray tube C2 having an oppositely located detector C3. Optionally there is disposed in the CT system shown here a second X-ray tube C4 having an oppositely located detector C5, such that a higher time resolution can be achieved by virtue of the additionally available emitter/detector combination; alternatively, if different X-ray energy spectra are used in the emitter/detector systems, "dual energy" examinations can also be carried out.

The CT system C1 also includes a patient couch C8 on which a patient can be moved along a system axis C9, also referred to as the z-axis, into the field of view in the course of the examination, the scanning itself being able to take place both as a pure circular scan without patient feed-through exclusively in the examination region of interest. The movement of the patient couch C8 relative to the gantry is effected with the aid of a suitable motorization means. During this movement the X-ray source C2 and/or C4 rotate/rotates around the patient in each case. In parallel the detector C3 or C5 in this case co-rotates opposite the X-ray source C2 or C4, respectively, in order to acquire projection measured data which is then used for reconstructing sectional images ("slices"). Alternatively to a sequential scan, in which the patient is moved incrementally through the examination field between the individual scans, it is, of course, also possible to perform a spiral scan, in which the patient is moved continuously along the system axis C9 through the examination field between X-ray tube C2 or C4 and detector C3 or C5, respectively, during the rotating scanning with the X-ray radiation. In a spiral scan the movement of the patient along the axis C9 and the simultaneous rotation of the X-ray source C2 or C4 results in the X-ray source C2 or C4 following a helical path relative to the patient during the measurement. This path can also be realized by moving the gantry along the axis C9 while the patient remains stationary. It is also possible to move the patient back and forth continuously and periodically between two points.

The CT system 10 is controlled by way of a control and computing unit C10 having computer program code Prg1 to Prgn residing in a memory. It is pointed out that the computer program codes Prg1 to Prgn can, of course, also be contained on an external storage medium and be loaded into the control and computing unit C10 as required.

Acquisition control signals AS can be transmitted from the control and computing unit C10 via a control interface 24 for the purpose of controlling the CT system C1 in accordance with specific measurement protocols. The acquisition control signals AS in this case relate e.g. to the X-ray tubes C2 and C4, in which case parameters relating to their power output and the times at which they are switched on and off can be defined, as well as to the gantry, in which case parameters relating to its speed of rotation can be defined, and to the table feed.

Since the control and computing unit C10 possesses an input console, measurement parameters can be entered by a user or operator of the CT scanner C1, which parameters can then control the data acquisition in the form of acquisition control signals AS. Information relating to currently used measurement parameters can be displayed on the screen of the control and computing unit C10; other relevant information for the operator can also be displayed.

The projection measured data p or raw data acquired by the detector C3 or C5 is passed via a raw data interface C23 to the control and computing unit C10. Following suitable preprocessing where necessary, the raw data p is then processed further in an image reconstruction component C21. In this example embodiment the image reconstruction component C21 is implemented in the control and computing unit C10 in the form of software on a processor, e.g. in the form of one or more of the computer program codes Prg1 to Prgn. With regard to the image reconstruction the same applies as already explained in relation to the control of the measurement process, namely that the computer program codes Prg1 to Prgn can also be contained on an external storage medium and can be loaded as required into the control and computing unit C10. It is also possible for the control of the measurement process and the image reconstruction to be performed by different computing units.

The image data f reconstructed by the image reconstruction component C21 is then stored in a memory C22 of the control and computing unit C10 and/or output in the usual way on the screen of the control and computing unit C10. The data can also be fed via an interface that is not shown in FIG. 1 into a network connected to the computed tomography system C1, a radiological information system (RIS) for example, and stored in a mass storage that is accessible there or can be output as images.

In addition the control and computing unit C10 can also perform the function of an ECG, a lead C12 being used to transmit the ECG potentials between patient and control and computing unit C10. In addition the CT system C1 shown in FIG. 1 also includes a contrast agent injector C11 via which contrast agent can additionally be injected into the patient's bloodstream so that e.g. the patient's vessels, in particular the ventricles of the beating heart, can be visualized more clearly. Furthermore there is also the possibility herewith to perform perfusion measurements, for which the proposed method is likewise suitable.

Figure 2:
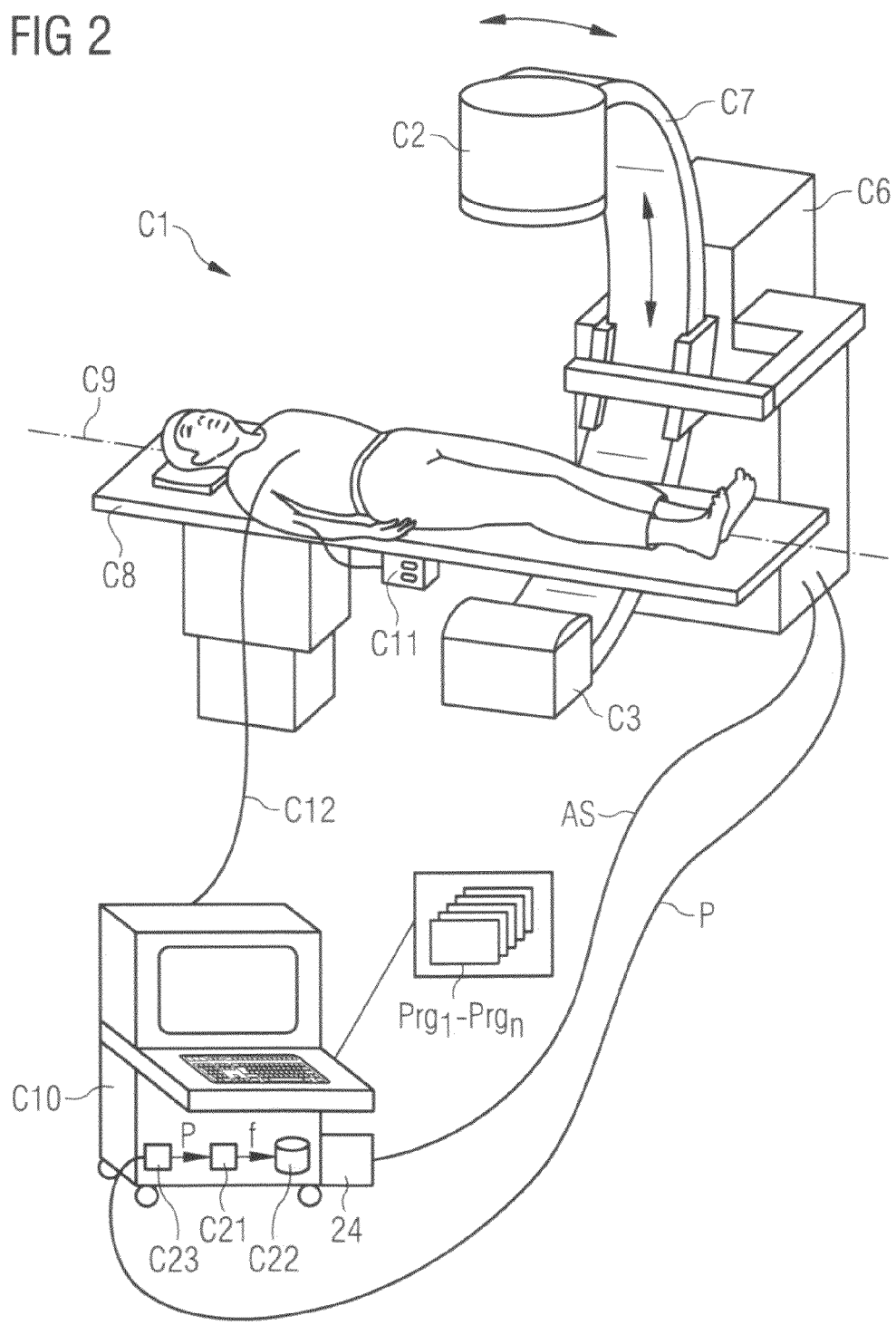
FIG. 2: shows a second schematic representation of an example embodiment of a computed tomography system having an image reconstruction component.

FIG. 2 shows a C-arm system in which, in contrast to the CT system shown in FIG. 1, the housing C6 carries the C-arm C7 to which the X-ray tube C2 is secured on one side and the oppositely located detector C3 is secured on the other. In order to perform a scan, the C-arm C7 is likewise pivoted around a system axis C9, such that scanning can take place from a plurality of scanning angles and corresponding projection data p can be determined from a plurality of projection angles. The C-arm system C1 shown in FIG. 2, like the CT system from FIG. 1, has a control and computing unit C10 of the type described with reference to FIG. 1.

Embodiments of the invention can be applied in both of the systems shown in FIGS. 1 and 2. Furthermore it can also be used in principle for other CT systems, e.g. for CT systems having a detector forming a complete ring.

The presence of a complete set of measured data is important for the image reconstruction. Complete, in this context, means that each volume element (voxel) of the examination subject which is to be included in the CT image must be irradiated over a projection angle range of 180°, for measurements in parallel beam geometry, or of 180° plus the cone vertex angle, for measurements in cone beam geometry, and the corresponding projections must be acquired by the detector. If these criteria are not met, although an image reconstruction is nevertheless possible, the resulting image will be laden with artifacts due to the incompleteness of the measured data sets.

Problems arise if the extent of the examination subject is greater than the field of view of the CT scanner. Such a situation is illustrated in FIG. 3. This shows a section from a CT scanner according to FIG. 1 or 2 which includes the X-ray source C2 and the detector C3. For improved clarity of illustration the detector C3 is shown with only twelve detector elements in the channel direction; in reality their number is considerably greater. The examination subject O is located between the X-ray source C2 and the detector C3. FIG. 3 shows a section normal to the z-axis; what can be seen, therefore, is an axial section through the examination subject O. At a specific projection angle, as shown in FIG. 3, the field of view FOV of the CT scanner in the section normal to the z-axis corresponds to a sector of a circle. Its edges are formed by the X-ray beams which travel from the X-ray source C2 to the outermost edges of the detector C3.

It is therefore the extent of the detector in the channel direction which determines the size of the field of view FOV. The channel direction in this case is the direction on the detector surface normal to the row direction. The row direction extends perpendicularly to the plane of the section of FIG. 3 and consequently along the z-direction. The detector dimension in the drawing plane of FIG. 3 is the channel direction.

It can be seen in FIG. 3 that at the projection angle shown the examination subject O does not lie completely within the field of view FOV. In the position of X-ray source C2 and detector C3 according to FIG. 3 the parts OA of the examination subject O are not illuminated by X-ray beams which are detected by the detector C3: the parts OA of the examination subject O lie outside the field of view FOV. If X-ray source C2 and detector C3 rotate around the examination subject O, then at some projection angles the parts OA of the examination subject O that lie outside the field of view FOV in the constellation according to FIG. 3 will lie within the field of view FOV, while for other projection angles they will lie outside the field of view FOV. This also applies similarly to the other edge regions of the examination subject O.

This means that no complete measured data set is present for some parts of the examination subject O. It generally holds that the overall field of view of the CT scanner, i.e. that area between X-ray source C2 and detector C3 for which complete data sets are acquired, is given by the intersection of the fan beams over a half-rotation of X-ray source C2 and detector C3 or, as the case may be, over a half-rotation of 180° plus the cone vertex angle. The extended field of view (eFOV) of the CT scanner is an area which includes the described area of the overall field of view, but is larger than this. Beyond the overall field of view the extended field of view includes those voxels which are illuminated only at some projection angles by X-ray beams which subsequently reach the detector.

For parts of the examination subject, such as e.g. the parts OA shown in FIG. 3, this means that information relating to said parts of the examination subject is included in the measured data in some of the recorded projections, whereas in other projections it is not. In relation to the parts of the examination subject which are located in the extended field of view, an incomplete data set is therefore present. This is also referred to as "limited angle" scanning.

An exceeding of the field of view by parts of an examination subject comes about in practice e.g. due to the corpulence of patients, or because a patient is not able to place his/her arms above or behind his/her head during a thorax measurement.

Since information relating to the examination subject is included within the extended field of view in some projections, it is not readily possible to reconstruct a CT image only for the area of the overall field of view. Rather, the exceeding of the field of view results in the CT image within the field of view being laden with artifacts. The reason for this is the above-explained incompleteness of the data of the extended field of view. The information of the extended field of view must rather be taken into account during the image reconstruction.

Different approaches exist for determining sufficiently good attenuation values for the extended field of view. On the one hand it would be possible to extend the field of view by increasing the size of the detector in the channel direction. However, this approach necessitates other types of detectors and an adaptation of the gantry, which is cost-intensive and therefore undesirable.

On the other hand software-based approaches exist for extrapolating projection data in the extended field of view outside the field of view from the measured values. For example, the measured data of the field of view can be mirrored into the extended field of view lying outside of the field of view and in the process be provided with a weighting factor. Depending on the object geometry the results are not always satisfactory due to the underdetermination of the mathematical problem. As a rule, however, qualitatively satisfactory image values at least within the field of view are obtained with such methods, whereas the image values outside the field of view are heavily artifact-laden and unreliable.

Such a possibility for image reconstruction in the extended field of view is described in the publication H. Bruder et al: "Efficient Extended Field-of-View (eFOv) Reconstruction Techniques for Multi-Slice Helical CT", Physics of Medical Imaging, SPIE Medical Imaging, Proceedings 2008, Vol. 9, No. 30, E2-13, the entire contents of which are hereby incorporated herein by reference.

In the following use is made of the knowledge that with known object geometry in the extended field of view largely correct and stable CT values can be reconstructed. The procedure in the course of the image reconstruction is explained with reference to the flowchart of FIG. 4.

Firstly, the measured data $p_{k,s,r}^{meas}$ (where the index k stands for the channel of the detector, the index s for the row of the detector, and the index r for the projection angle) is used in step eFOV Recon in order to perform a conventional image reconstruction in the extended field of view. The method presented in the above-cited publication can be used for this purpose, for example. An image of the examination subject both within the overall field of view and within the extended field of view going beyond the former is therefore present as the result of the step eFOV Recon.

In the following step boun, this reconstructed image is used in order to determine the contours, in other words the boundary of the examination subject. This can be effected e.g. with the aid of threshold value formation, i.e. all pixels whose CT values exceed a threshold value are attributed to the examination subject. Other segmentation methods are also possible. A CT image which indicates the contours of the examination subject is therefore present as the result of step boun.

In step be1, all pixels lying outside the overall field of view and within the extended field of view are assigned a constant CT value. A suitable example is the CT value of water. The CT values of the pixels within the field of view are not changed. A modified CT image of the examination subject is therefore present as the result of step be1.

In the following step data, projection values are calculated from the modified image of step be1. It is therefore calculated which measured values would lead to the modified image. These synthetic measured values are obtained by means of a forward projection, the scan geometry being included in this calculation. An example of a scan geometry is a spiral scan with a multirow detector. The projection data set $p_{k,s,r}^{proj}$ is obtained as the result of step data.

In addition to step data, FIG. 4 shows data in a sinogram space. The sinogram represents a two-dimensional space per detector row, which space is spanned on the one side by the projection angle, i.e. the angular position of the X-ray source relative to the examination subject, and on the other side by the fan angle within the X-ray beam, i.e. by the position of the detector pixel in the channel direction. The sinogram space therefore represents the domain of the measured data, whereas the image space represents the domain of the image data. By means of a back-projection a transition is made from the sinogram space into the image space, i.e. from the measured data to the image data, and vice versa by way of a forward projection. The sinogram schematically shows that following step data, projection values are also present for the extended field of view, which corresponds to the two strips on the right- and left-hand edge of the sinogram.

In step data*, the projection data calculated in step data is supplemented in accordance with formula (1). The corrected projection data set $p_{k,s,r}^{korr}$ is present as the result.

$$p_{k,s,r}^{korr} = \lambda_k \cdot p_{k,s,r}^{meas} + (1-\lambda_k) \cdot p_{k,s,r}^{proj} \qquad \text{Formula (1)}$$

The mixing function $\lambda_k$ is calculated as follows:

$$\lambda_k = \begin{cases} 1 & m+z < k < n-z \\ \cos^2 \dfrac{\pi}{2} \dfrac{k-m}{n-k} & m \le k \le m+z \land n-z \le k \le n \\ 0 & k < m \land k > n \end{cases} \qquad \text{Formula (2)}$$

where it holds that $$m = \frac{k_{eFOV} - k_{FOV}}{2}$$

and $$n = \frac{k_{eFOV} + k_{FOV}}{2};$$

m and n are fixed quantities. The value of the mixing function $\lambda_k$ is therefore dependent only on k, the channel index. $k_{FOV}$ denotes the number of channels in the field of view, and $k_{eFOV}$ denotes the number of channels in the extended field of view. For example, $k_{FOV}$ can equal 736, i.e. each detector row has 736 detector elements, and $k_{eFOV}$ 1000. In this case the extended field of view would extend by 132 detector elements on both sides of the field of view.

z is a small fixed quantity, e.g. 20. It corresponds to a transition zone, as will be explained below.

FIG. 5 shows an illustration to aid understanding of the formulae (1) and (2). What is shown is the extent of a detector row. The number $k_{FOV}$ of channels of the field of view is contained in the central area. At the edge, m channels in each case join on at the right-hand and left-hand side, said channels m forming the $k_{eFOV}$ channels of the extended field of view in combination with the $k_{FOV}$ channels of the field of view. Starting from the left-hand edge of the row, the field of view begins after m channels and ends after n channels.

If the channel index k is less than m or greater than n (lower case of formula (2)), this corresponds to the channels of the extended field of view outside the field of view. For this case the mixing function is equal to zero. This means that $p_{k,s,r}^{korr}$ is equal to $p_{k,s,r}^{proj}$. Outside of the field of view, therefore, only the calculated projection data $p_{k,s,r}^{proj}$ is used for the image reconstruction.

If the channel index k lies between m and n, or more precisely is removed by a distance of z from the limits m and n (upper case of formula (2)), this corresponds to the inner channels of the field of view. In this case the mixing function is equal to one. This means that $p_{k,s,r}^{korr}$ is equal to $p_{k,s,r}^{meas}$. Inside the field of view, therefore, only the measured projection data $p_{k,s,r}^{meas}$ is used for the image reconstruction.

In the transition zone, namely between m and m+z, as well as between n−z and n, the squared cosine function of the middle line of formula (2) effects a soft transition between 1 and 0. In this zone there is therefore yielded a mixture composed of the measured values $p_{k,s,r}^{meas}$ and the calculated values $p_{k,s,r}^{proj}$.

The measured data $p_{k,s,r}^{corr}$ corrected according to formula (1) is used in the following step Recon in order to reconstruct a CT image of the examination subject within the extended field of view using an algorithm known per se, e.g. based on a Feldkamp-like algorithm.

Figures 6A, 6B:
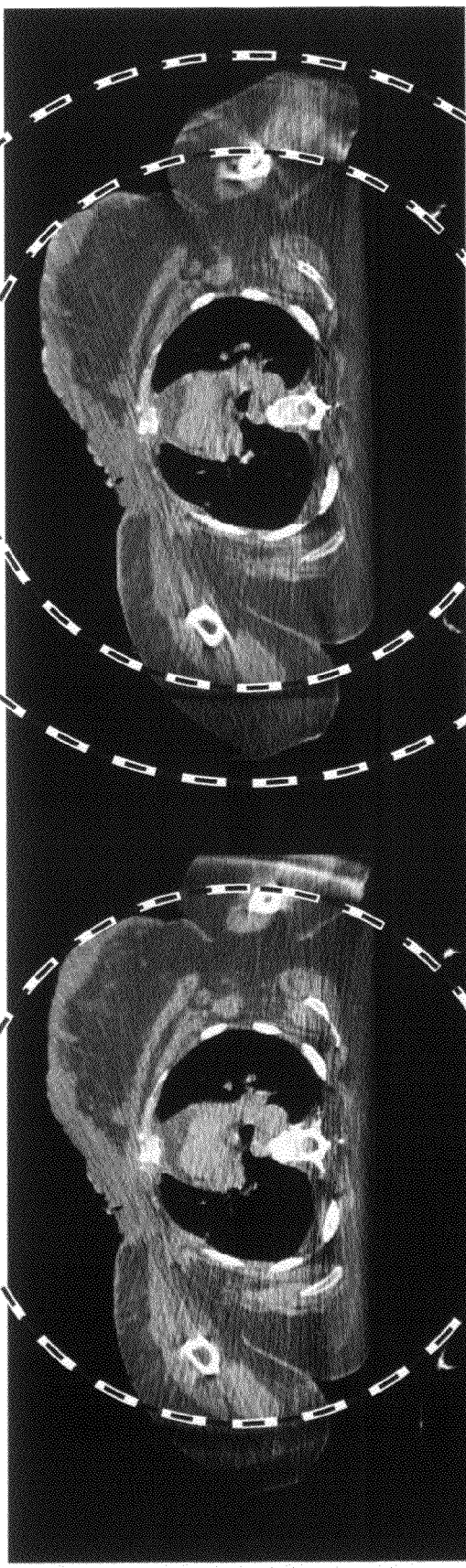
FIG. 6: shows two CT images.

The result of an image reconstruction of this kind is shown in FIG. 6. FIG. 6A shows a tomographic slice through the upper body of a patient. The limit of the field of view is indicated by the dashed circle. It can clearly be seen, in particular on the right-hand side, that the image is truncated and of poor quality. For FIG. 6B, a CT image has been reconstructed in accordance with above-explained method, based on the same data set from which the CT image of FIG. 6A was computed. It can be seen that useful CT values have been determined beyond the field of view (inner circle with diameter 50 cm) in an extended area (outer circle with diameter 70 cm).

The invention has been described in the foregoing with reference to an exemplary embodiment. It is to be understood that numerous variations and modifications are possible without leaving the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:
reconstructing first image data from the measured data;
determining a boundary of the examination subject with an aid of the first image data;
modifying the first image data using the determined boundary;
calculating projection data from the modified first image data;
modifying the measured data using the calculated projection data; and
reconstructing second image data from the modified measured data, wherein pixel values of pixels within the determined boundary and outside the field of view are changed in the course of the modification of the first image data, and said pixel values are assigned a constant value.

2. A control and computing unit for reconstructing image data of an examination subject from measured data of a CT system, comprising:
a program memory, storing program code to, when executed, perform the method as claimed in claim 1.

3. A CT system comprising:
the control and computing unit as claimed in claim 2.

4. The method as claimed in claim 1, wherein only the pixel values of said pixels are changed in the course of the modification of the first image data.

5. A computer program comprising program code segments for performing the method as claimed in claim 1 when the computer program is executed on a computer.

6. A computer program product, comprising program code segments of a computer program, stored on a non-transitory computer-readable data medium, for performing the method as claimed in claim 1 when the computer program is executed on a computer.

7. A non-transitory computer readable medium including program segments for, when executed on a computer device, causing the computer device to implement the method of claim 1.

8. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:
reconstructing first image data from the measured data;
determining a boundary of the examination subject with an aid of the first image data;
modifying the first image data using the determined boundary;
calculating projection data from the modified first image data;
modifying the measured data using the calculated projection data; and
reconstructing second image data from the modified measured data, wherein
pixel values of pixels within the determined boundary and outside the field of view are changed in the course of the modification of the first image data, and
only the pixel values of said pixels are changed in the course of the modification of the first image data.

9. A control and computing unit for reconstructing image data of an examination subject from measured data of a CT system, comprising:
a program memory, storing program code to, when executed, perform the method as claimed in claim 8.

10. A computer program comprising program code segments for performing the method as claimed in claim 8 when the computer program is executed on a computer.

11. A computer program product, comprising program code segments of a computer program, stored on a non-transitory computer-readable data medium, for performing the method as claimed in claim 8 when the computer program is executed on a computer.

12. A non-transitory computer readable medium including program segments for, when executed on a computer device, causing the computer device to implement the method of claim 8.

13. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:
reconstructing first image data from the measured data;
determining a boundary of the examination subject with an aid of the first image data;
modifying the first image data using the determined boundary;
calculating projection data from the modified first image data;
modifying the measured data using the calculated projection data; and
reconstructing second image data from the modified measured data,
wherein the boundary of the examination subject is determined using a threshold value comparison of pixel values of the first image data.

14. The method as claimed in claim 13, wherein in the course of the modification of the measured data, use is made of the following formula:

$$p_{k,s,r}^{korr} = \lambda_k p_{k,s,r}^{meas} + (1-\lambda_k) \cdot p_{k,s,r}^{proj}$$

where
$p_{k,s,r}^{korr}$ denotes the modified measured data
$p_{k,s,r}^{korr}$ denotes the measured data
$p_{k,s,r}^{korr}$ denotes the projection data
k denotes the channel index of the detector s denotes the row index of the detector r denotes the projection angle index $\lambda_k$ denotes a quantity between 0 and 1 that is variable by way of the channel index.

15. A computer program comprising program code segments for performing the method as claimed in claim 13 when the computer program is executed on a computer.

16. A computer program product, comprising program code segments of a computer program, stored on a non-transitory computer-readable data medium, for performing the method as claimed in claim 13 when the computer program is executed on a computer.

17. The method as claimed in claim 13, wherein pixel values of pixels within the determined boundary and outside the field of view are changed in the course of the modification of the first image data.

18. The method as claimed in claim 17, wherein said pixel values are assigned a constant value.

19. The method as claimed in claim 18, wherein only the pixel values of said pixels are changed in the course of the modification of the first image data.

20. A non-transitory computer readable medium including program segments for, when executed on a computer device, causing the computer device to implement the method of claim 13.

21. A control and computing unit for reconstructing image data of an examination subject from measured data of a CT system, comprising: a program memory, storing program code to, when executed, perform the method as claimed in claim 13.

22. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:

reconstructing first image data from the measured data;

determining a boundary of the examination subject with an aid of the first image data;

modifying the first image data using the determined boundary;

calculating projection data from the modified first image data;

modifying the measured data using the calculated projection data; and reconstructing second image data from the modified measured data, wherein in the course of the modification of the measured data for at least one area outside the detector, the respective projection data is used as data on which the reconstruction of the second image data is to be based.

23. A control and computing unit for reconstructing image data of an examination subject from measured data of a CT system, comprising:

a program memory, storing program code to, when executed, perform the method as claimed in claim 22.

24. A computer program comprising program code segments for performing the method as claimed in claim 22 when the computer program is executed on a computer.

25. A computer program product, comprising program code segments of a computer program, stored on a non-transitory computer-readable data medium, for performing the method as claimed in claim 22 when the computer program is executed on a computer.

26. A non-transitory computer readable medium including program segments for, when executed on a computer device, causing the computer device to implement the method of claim 22.

27. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:

reconstructing first image data from the measured data;

determining a boundary of the examination subject with an aid of the first image data;

modifying the first image data using the determined boundary;

calculating projection data from the modified first image data;

modifying the measured data using the calculated projection data; and reconstructing second image data from the modified measured data, wherein in the course of the modification of the measured data for at least one area of the detector, the respective measured data is regarded as data on which the reconstruction of the second image data is to be based.

28. A control and computing unit for reconstructing image data of an examination subject from measured data of a CT system, comprising:

a program memory, storing program code to, when executed, perform the method as claimed in claim 27.

29. A computer program comprising program code segments for performing the method as claimed in claim 27 when the computer program is executed on a computer.

30. A computer program product, comprising program code segments of a computer program, stored on a non-transitory computer-readable data medium, for performing the method as claimed in claim 27 when the computer program is executed on a computer.

31. A non-transitory computer readable medium including program segments for, when executed on a computer device, causing the computer device to implement the method of claim 27.

32. A method for reconstructing image data of an examination subject from measured data, wherein the measured data was acquired in the course of a relative rotational movement between a radiation source of a computed tomography system and the examination subject, and wherein a limited area between the radiation source and a detector represents a field of view in respect of which measured data is acquireable, and wherein parts of the examination subject were located at least temporarily outside the field of view during the measured data acquisition, the method comprising:

reconstructing first image data from the measured data;

determining a boundary of the examination subject with an aid of the first image data;

modifying the first image data using the determined boundary;

calculating projection data from the modified first image data;

modifying the measured data using the calculated projection data; and reconstructing second image data from the modified measured data, wherein in the course of the modification of the measured data for at least one area at the edge of the detector, a combination of the respective measured data and the respective projection data is regarded as data on which the reconstruction of the second image data is to be based.

33. A control and computing unit for reconstructing image data of an examination subject from measured data of a CT system, comprising:

a program memory, storing program code to, when executed, perform the method as claimed in claim 32.

34. A computer program comprising program code segments for performing the method as claimed in claim 32 when the computer program is executed on a computer.

35. A computer program product, comprising program code segments of a computer program, stored on a non-transitory computer-readable data medium, for performing the method as claimed in claim 32 when the computer program is executed on a computer.

36. A non-transitory computer readable medium including program segments for, when executed on a computer device, causing the computer device to implement the method of claim 32.

* * * * *